(12) United States Patent
Tanaka et al.

(10) Patent No.: US 8,677,989 B2
(45) Date of Patent: Mar. 25, 2014

(54) NEBULIZER KIT AND NEBULIZER

(75) Inventors: Shinya Tanaka, Mishima-gun (JP); Susumu Kutsuhara, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/642,415

(22) PCT Filed: Mar. 1, 2011

(86) PCT No.: PCT/JP2011/054595
§ 371 (c)(1),
(2), (4) Date: Oct. 19, 2012

(87) PCT Pub. No.: WO2011/135915
PCT Pub. Date: Nov. 3, 2011

(65) Prior Publication Data
US 2013/0037020 A1 Feb. 14, 2013

(30) Foreign Application Priority Data

Apr. 28, 2010 (JP) ................................. 2010-103126

(51) Int. Cl.
*A61M 11/00* (2006.01)
(52) U.S. Cl.
USPC ............ 128/200.21; 128/200.18; 128/203.12; 206/438
(58) Field of Classification Search
USPC ............ 128/200.12, 200.16, 200.17, 200.18, 128/200.21, 203.12, 203.15; 604/317; 220/603, 719, 731; 222/571; 239/343
See application file for complete search history.

(56) References Cited

U.S. PATENT DOCUMENTS

| | | | | |
|---|---|---|---|---|
| 5,054,477 | A * | 10/1991 | Terada et al. | 128/200.14 |
| 5,752,505 | A * | 5/1998 | Ohki et al. | 128/203.15 |
| 6,085,741 | A * | 7/2000 | Becker | 128/200.14 |
| 7,568,480 | B2 * | 8/2009 | Foley et al. | 128/200.24 |
| 2003/0136399 | A1 | 7/2003 | Foley et al. | |
| 2008/0083409 | A1 * | 4/2008 | Hamaguchi et al. | 128/200.24 |

(Continued)

FOREIGN PATENT DOCUMENTS

| | | |
|---|---|---|
| CN | 101277731 A | 10/2008 |
| JP | 06-285168 A | 10/1994 |

(Continued)

OTHER PUBLICATIONS

Official Communication issued in International Patent Application No. PCT/JP2011/0545945, mailed on Mar. 29, 2011.

(Continued)

*Primary Examiner* — Steven Douglas
(74) *Attorney, Agent, or Firm* — Keating & Bennett, LLP

(57) ABSTRACT

A nebulizer kit includes a case body, a flow channel formation member that covers an opening of the case body, an outside air introduction tube erected vertically from a base surface of the flow channel formation member and including a long groove formed in an inner circumferential surface thereof, a compressed air introduction tube below the outside air introduction tube within the case body and extending toward the interior of the outside air introduction tube, and an atomizing area formation member. The atomizing area formation member includes a liquid suction tube formation portion, a baffle, and a baffle support portion that connects the liquid suction tube formation portion and the baffle and that extends toward a side area of the baffle from an outer surface of the liquid suction tube formation portion. The baffle support portion is contained within the long groove of the outside air introduction tube.

6 Claims, 7 Drawing Sheets

(56) References Cited

U.S. PATENT DOCUMENTS

2010/0147292 A1    6/2010   Hamaguchi et al.
2010/0319687 A1   12/2010   Esaki et al.

FOREIGN PATENT DOCUMENTS

| JP | 2006-255308 A | 9/2006 |
| JP | 2007-097830 A | 4/2007 |
| JP | 2009-219543 A | 10/2009 |

OTHER PUBLICATIONS

Official Communication issued in corresponding Chinese Patent Application No. 201180021455.6, mailed on Nov. 4, 2013.

* cited by examiner

NEBULIZER KIT AND NEBULIZER

BACKGROUND OF THE INVENTION

1. Field of the Invention

The present invention relates to nebulizer kits and nebulizers.

2. Description of the Related Art

A nebulizer is a device for producing an aerosol by atomizing a liquid such as water, a saline solution, a drug solution for treating respiratory system conditions, or the like. Normally, a nebulizer includes a nebulizer kit that produces the aerosol. JP H6-285168A or JP 2009-219543A are examples of background art documents disclosing nebulizer kits.

A typical nebulizer kit 1000 will be described hereinafter with reference to FIG. 8. In the nebulizer kit 1000, an atomizing area formation member 220 is contained and disposed within a case body 210. The atomizing area formation member 220 includes: a conical liquid suction tube formation portion 224 in whose apex is formed an opening portion 224*a*; a baffle 222 located immediately above the opening portion 224*a*; and a baffle support portion 223 that extends from the outer surface of the liquid suction tube formation portion 224 toward the sides of the baffle 222.

An outside air introduction tube 234 that is linked to an opening portion in an aerosol discharge port 232 is provided in the base of a flow channel formation member 230 attached to an upper area of the case body 210. An atomizing area M is formed between an upper leading end 214*a* of a compressed air introduction tube 214 and the baffle 222. At the atomizing area M, compressed air introduced from the compressed air introduction tube 214 is blown from the upper leading end 214*a* of the compressed air introduction tube 214 toward the baffle 222.

At this time, a liquid (not shown) sucked upward to the vicinity of the atomizing area M from a reservoir portion 216 due to the effects of negative pressure produced at the atomizing area M is blown upward toward the atomizing area M due to the effects of the negative pressure and is blown toward the baffle 222 along with the compressed air. Due to these effects, a liquid W turns into fine liquid droplets upon colliding with the baffle 222, becoming mist particles as a result; these mist particles are added to the outside air introduced into the case body 210, thus producing an aerosol within the case body 210. The aerosol is discharged toward the aerosol discharge port 232, and is then further discharged to the exterior from the aerosol discharge port 232.

However, when the atomizing area formation member 220 is contained and disposed within the case body 210, the baffle support portion 223 has been located further inward in the diametrical direction than the inner circumferential surface 236 of the outside air introduction tube 234, which is formed in a cylindrical shape. For this reason, there is a problem in that a large amount of mist particles or aerosol produced at the atomizing area M collects on the areas formed by the baffle support portion 223 and the inner circumferential surface 236 of the outside air introduction tube 234, which has resulted in a drop in the efficiency with which the aerosol is produced and discharged. Thus, the aerosol could not be efficiently produced and discharged.

SUMMARY OF THE INVENTION

Accordingly, preferred embodiments of the present invention provide a nebulizer kit and a nebulizer that efficiently produce and discharge an aerosol.

A nebulizer kit according to a preferred embodiment of the present invention includes a closed-ended, approximately cylindrical case body, a cover-shaped flow channel formation member, an outside air introduction tube, a compressed air introduction tube, and an atomizing area formation member. The case body includes an opening in an upper end, and an aerosol is produced within the case body. The flow channel formation member is attached so as to cover the opening. The outside air introduction tube is provided within the case body so as to hang downward from a base surface of the flow channel formation member, and includes a long groove formed in an inner circumferential surface. The compressed air introduction tube is provided below the outside air introduction tube within the case body, and includes an upper leading end area that extends toward the interior of the outside air introduction tube. The atomizing area formation member includes a liquid suction tube formation portion including an opening portion formed in the apex thereof, a baffle located above the opening portion, and a baffle support portion that extends from an outer surface of the liquid suction tube formation portion toward a side area of the baffle.

The baffle support portion is contained within the long groove of the outside air introduction tube so that the flow channel formation member is attached to the case body and the liquid suction tube formation portion of the atomizing area formation member is mounted so as to cover the upper leading end area of the compressed air introduction tube.

In a nebulizer kit according to another preferred embodiment of the present invention, a surface on the inner peripheral side of the baffle support portion and the inner circumferential surface of the outside air introduction tube are approximately flush when the baffle support portion is contained within the long groove of the outside air introduction tube.

In a nebulizer kit according to yet another preferred embodiment of the present invention, the outer shape of the baffle support portion preferably corresponds to the shape of the inner peripheral surface of the long groove. Furthermore, the baffle support portion is preferably fitted into the long groove when the baffle support portion is contained within the long groove.

A nebulizer according to a preferred embodiment of the present invention includes a main body, a compressed air tube portion, and a nebulizer kit according to a preferred embodiment of the present invention that produces an aerosol. The main body includes a compressor that discharges compressed air. The compressed air tube portion is a portion through which the compressed air discharged by the compressor is led. One end of the compressed air tube portion is connected to the nebulizer kit.

According to the nebulizer and the nebulizer kit according to various preferred embodiments of the present invention, it is possible to provide a nebulizer kit and a nebulizer capable of efficiently producing and discharging an aerosol.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
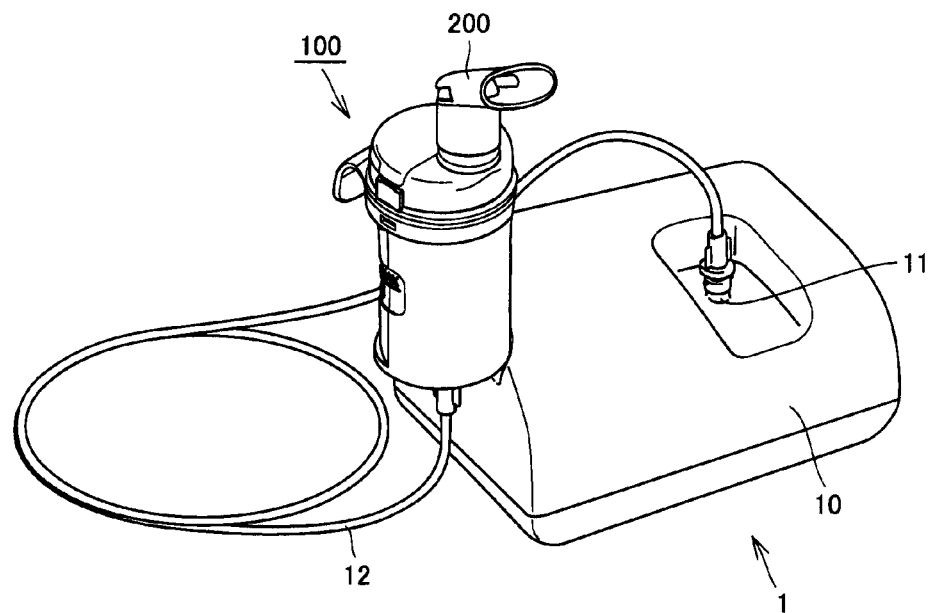
FIG. 1 is an overall perspective view illustrating the external configuration of a nebulizer according to a preferred embodiment of the present invention.

Hereinafter, a nebulizer kit and a nebulizer according to preferred embodiments of the present invention will be described in detail with reference to the drawings. When numbers, amounts, and so on are discussed in the following preferred embodiments, it should be noted that unless explicitly mentioned otherwise, the scope of the present invention is not necessarily limited to those numbers, amounts, and so on. In the drawings, identical reference numerals refer to identical or corresponding elements; there are also cases where redundant descriptions are omitted.

Hereinafter, a nebulizer 1 and a nebulizer kit 100 according to a preferred embodiment will be described with reference to FIGS. 1 through 7. First, outlines of the configurations of the nebulizer 1 and the nebulizer kit 100 will be described.

As shown in FIG. 1, the nebulizer 1 preferably includes: a main body 10 that contains a compressor that emits compressed air, electrical components, and so on; a tube 12, serving as a flexible compressed air tube portion, whose one end is connected to a compressed air expulsion port 11 provided in the main body 10; the nebulizer kit 100, to which the other end of the tube 12 is connected; and a mouthpiece 200 that is connected to the nebulizer kit 100 and that serves as an inhalation assistance tool to assist a user to inhale from his or her mouth, nose, or the like. Various types of shapes are possible for the mouthpiece 200, such as a mask shape, for example.

Figure 2:
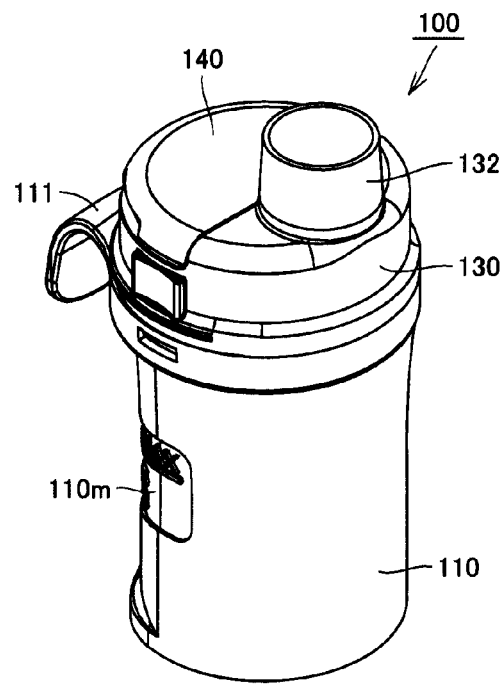
FIG. 2 is a first overall perspective view illustrating the external configuration of a nebulizer kit according to a preferred embodiment of the present invention.
Figure 3:
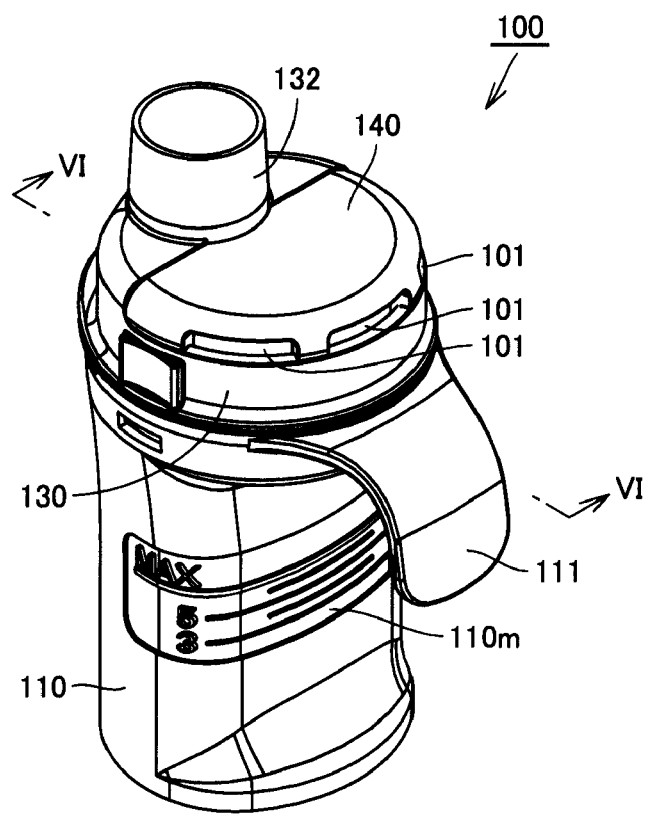
FIG. 3 is a second overall perspective view illustrating the external configuration of a nebulizer kit according to a preferred embodiment of the present invention.
Figure 4:
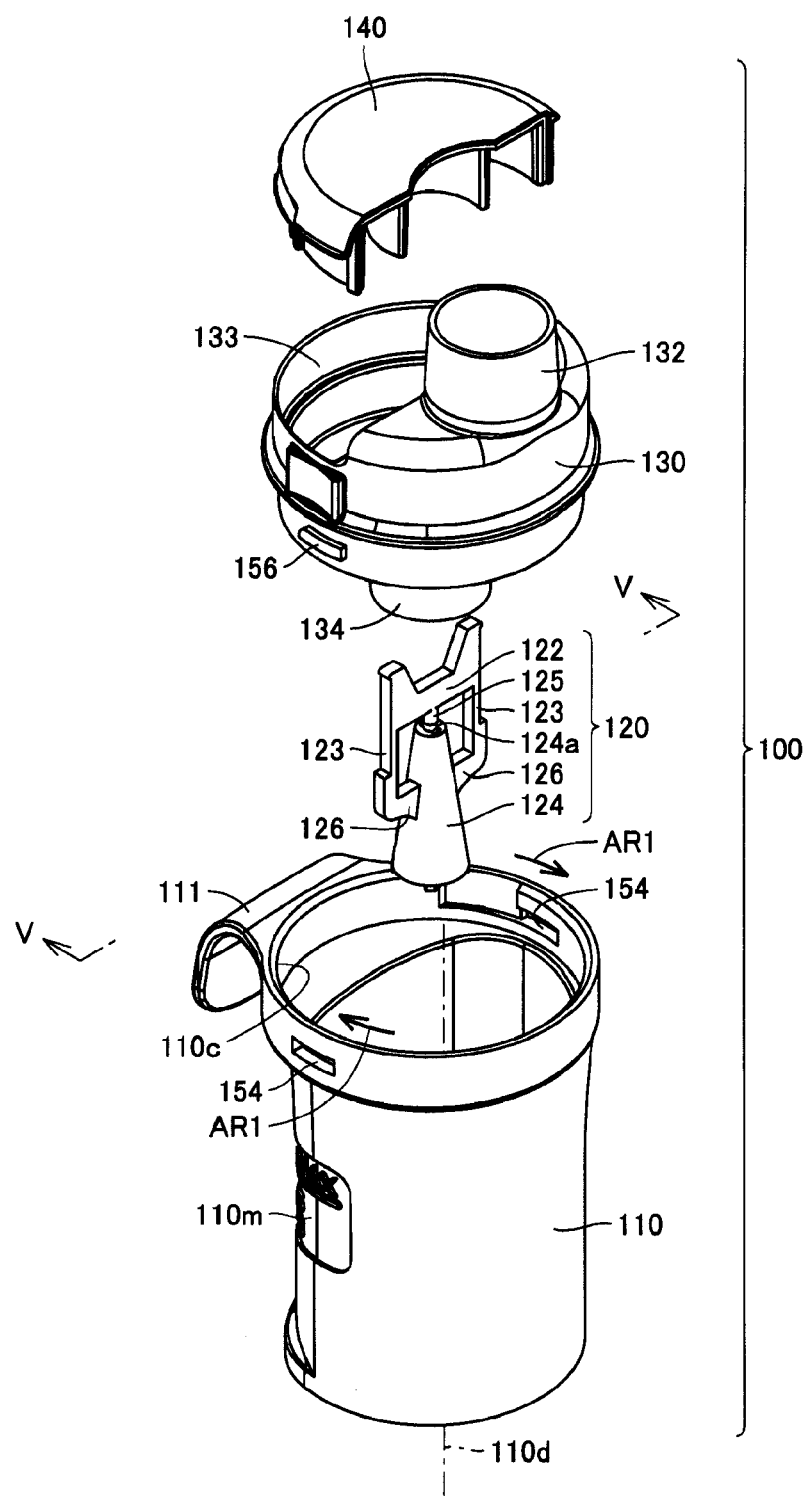
FIG. 4 is an exploded perspective view illustrating the nebulizer kit according to a preferred embodiment of the present invention.

As shown in FIGS. 2 through 4, the nebulizer kit 100 preferably includes a case body 110, an atomizing area formation member 120 (see FIG. 4), a flow channel formation member 130, and a cap member 140. A cylindrical aerosol discharge port 132 is provided in the top surface of the flow channel formation member 130 so as to pass through a portion of the top surface of the flow channel formation member 130, and an inhalation assistance tool such as the mouthpiece 200 (see FIG. 1) is connected to this aerosol discharge port 132.

As shown in FIG. 3, a grip 111 is provided on the outer surface of the case body 110. The grip 111 extends outward from the stated outer surface in the diametric direction of the case body 110, and is configured so that the leading end side thereof curves downward.

A scale 110m to b used to confirm the amount of a liquid such as a drug solution that is contained within the case body 110 is provided in the outer surface of the case body 110 below the grip 111. The scale 110m is provided on a wall surface of the case body 110 that faces outward so that the amount of liquid (that is, the content displayed by the scale 110m) can be easily seen from outside the case body 110. It is preferable to set the positional relationship between the grip 111 and the scale 110m so that the scale 110m is not visually obstructed by the grip 111. For example, it is preferable for the stated positional relationship to be set so that when the grip 111 is projected toward the side wall of the case body 110, the resulting projected image does not overlap with the scale 110m (see FIG. 3). Multiple pressure adjustment spaces 101 are formed between the cap member 140 and the flow channel formation member 130.

Figure 5:
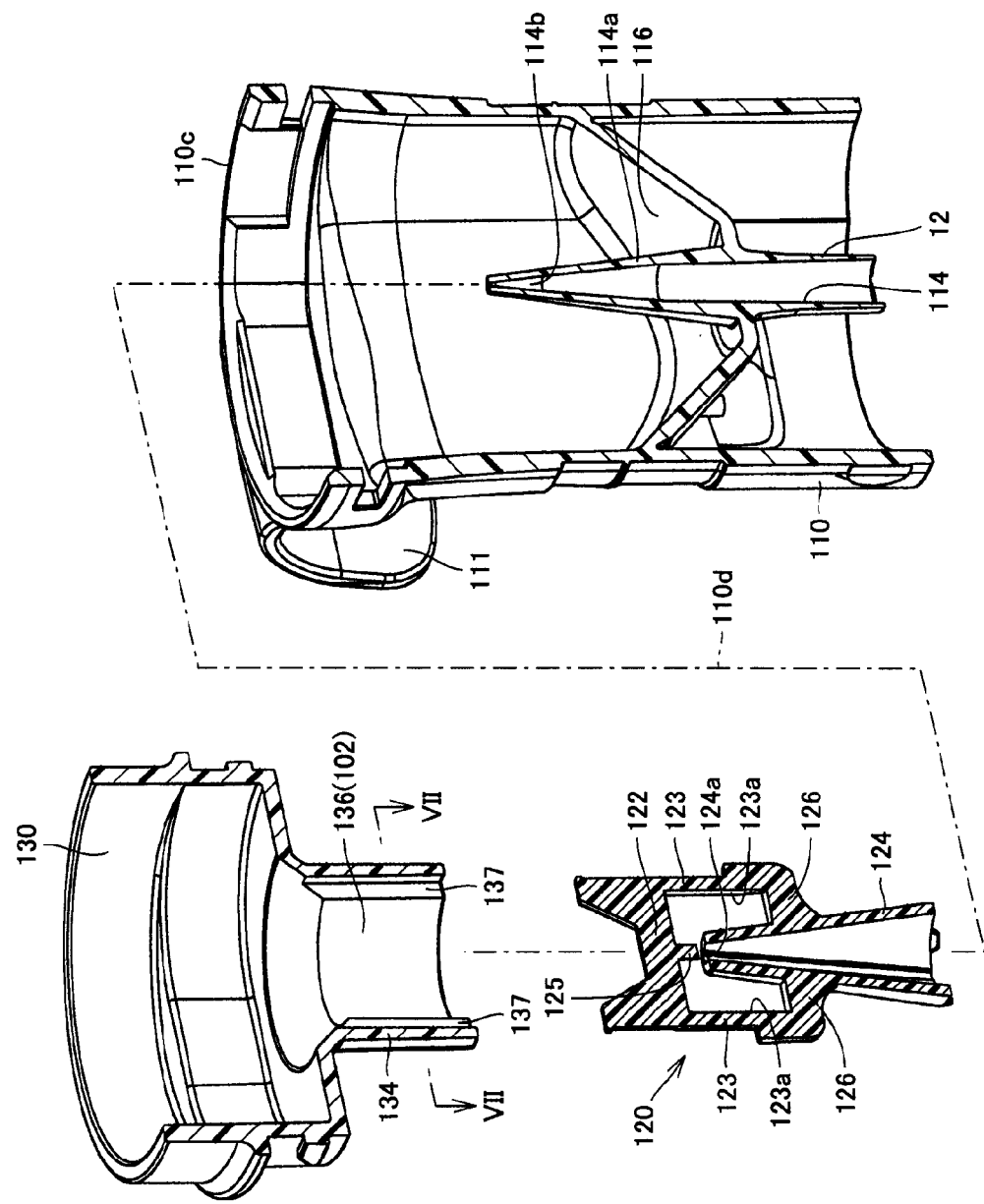
FIG. 5 is a vertical cross-sectional view taken along the V-V arrow in FIG. 4.

As shown in FIGS. 4 and 5, the atomizing area formation member 120 preferably includes: a conical liquid suction tube formation portion 124 that includes an opening portion 124a formed in the apex thereof; a baffle 122 located immediately above the opening portion 124a; baffle support portions 123 that extend from the outside surface of the liquid suction tube formation portion 124 (that is, an arm portion 126) toward a side area of the baffle 122; and a protrusion 125 provided below the center of the baffle 122. The baffle support portions 123 connect the baffle 122 to the outside surface of the liquid suction tube formation portion 124 (that is, the arm portion 126).

The case body 110 includes an opening 110c at the upper end thereof, and is configured as a closed-ended cylinder. The atomizing area formation member 120 is contained and disposed within the case body 110. An engagement recess 154 (see FIG. 4) is provided on the inner circumferential surface of the case body 110 toward the opening 110c, so as to extend along the circumferential direction.

The flow channel formation member 130 preferably has a cover-like shape, and a protrusion 156 (see FIG. 4) is provided in the outer circumferential surface at the lower end thereof, so as to extend along the circumferential direction. The flow channel formation member 130 is fitted into the upper area of the case body 110 so as to cover the opening 110c in the upper end of the case body 110.

The protrusion 156 and the engagement recess 154 are engaged with each other by rotating the flow channel formation member 130 in the direction of an arrow AR1 while the flow channel formation member 130 is fitted into the case body 110. The flow channel formation member 130 is attached to the upper area of the case body 110 through this engagement. The cap member 140 is then attached to the flow channel formation member 130 so as to cover an opening portion 133 provided in the top surface of the flow channel formation member 130.

Figure 6:
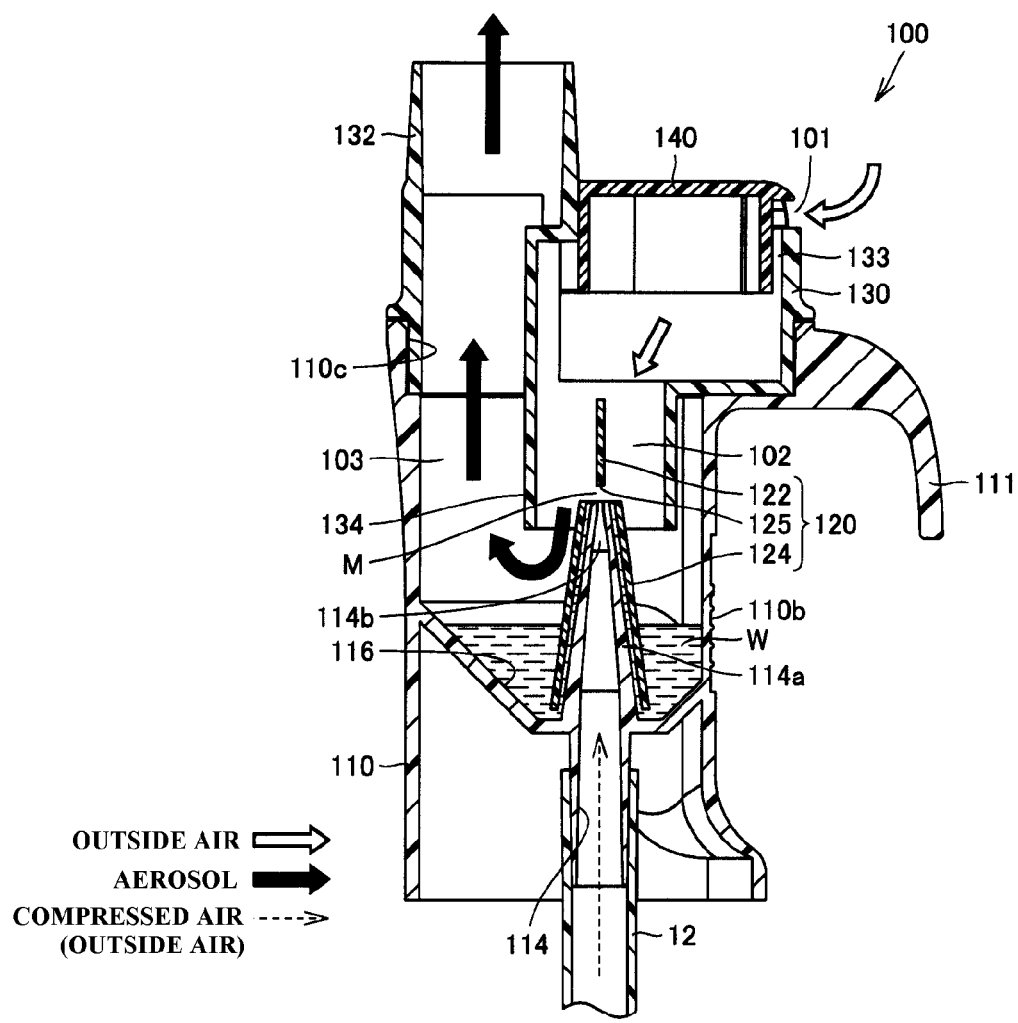
FIG. 6 is a vertical cross-sectional view taken along the VI-VI line in FIG. 3.

As shown in FIG. 6, the aerosol discharge port 132 is provided in a location of the top surface of the flow channel formation member 130 that is offset toward the outside in the radial direction (to the left, in the drawings). The case body 110, the atomizing area formation member 120, the flow channel formation member 130, the cap member 140, and the tube 12 can be separated from each other and reassembled, and the configuration is therefore such that the nebulizer 1 can be washed and sterilized with ease after use. Furthermore, the inhalation assistance tool, such as the mouthpiece 200, is a disposable type, and is discarded after use for sanitary reasons.

As shown in FIG. 6, an outside air introduction tube 134 that connects to an opening portion of the aerosol discharge port 132 is provided in the base surface of the flow channel formation member 130. A compressed air introduction tube 114 used to introduce compressed air discharged from a compressor through the compressed air expulsion port 11 (see FIG. 1) and the tube 12 into the interior of the case body 110 is provided in the base surface of the case body 110 so as to extend in the vertical direction.

The tube 12 is attached to the lower leading end area of the compressed air introduction tube 114. Meanwhile, an upper leading end area 114a of the compressed air introduction tube 114 preferably has a shape that tapers toward a leading end opening 114b.

A reservoir portion 116 is provided in the periphery of the area of the case body 110 where the compressed air introduction tube 114 is located. The reservoir portion 116 temporarily holds a liquid W such as water, a saline solution, a drug solution for treating respiratory system conditions or the like, a vaccine, or the like.

The liquid suction tube formation portion 124 of the atomizing area formation member 120 is mounted so as to cover the upper leading end area 114a of the compressed air introduction tube 114; the leading end opening 114b of the compressed air introduction tube 114 is exposed from the opening portion 124a of the liquid suction tube formation portion 124, and opposes the protrusion 125 of the baffle 122 in the atomizing area formation member 120.

Next, the production and discharge of aerosol will be described with reference to FIG. 6. Note that in FIG. 6, the broken line arrow indicates the flow of compressed air (outside air) discharged from the main body 10 (see FIG. 1) of the nebulizer 1, the white arrow indicates the flow of outside air introduced from the pressure adjustment spaces 101, and the black arrow indicates the discharge flow of the aerosol.

A liquid suction tube preferably includes the gap between the liquid suction tube formation portion 124 and the upper leading end area 114a of the compressed air introduction tube 114, and the liquid W held in the reservoir portion 116 reaches the vicinity of an atomizing area M, which will be mentioned later, under the effect of a negative pressure caused by the blowing of the compressed air, which will also be mentioned later.

The atomizing area M is located between the upper leading end area 114a of the compressed air introduction tube 114 and the protrusion 125 of the baffle 122. At the atomizing area M, compressed air introduced into the compressed air introduction tube 114 by the main body 10 of the nebulizer 1 is blown from the upper leading end area 114a of the compressed air introduction tube 114 toward the protrusion 125 of the baffle 122. At this time, the liquid W sucked upward to the vicinity of the atomizing area M due to the effects of negative pressure produced at the atomizing area M is blown upward toward the atomizing area M due to the stated effects of the negative pressure and is blown toward the protrusion 125 of the baffle 122 along with the compressed air.

Due to these effects, the liquid W turns into fine liquid droplets upon colliding with the protrusion 125 of the baffle 122, becoming mist particles as a result; these mist particles are added to the outside air introduced into the case body 110 (this includes outside air introduced by the main body 10 of the nebulizer 1 as mentioned above, as well as outside air introduced from the pressure adjustment spaces 101 (mentioned later) based on suction actions performed by a user), thus producing an aerosol within the case body 110.

The flow channel formation member 130 and the cap member 140 are positioned and disposed above the atomizing area formation member 120. The inner space of the case body 110 is partitioned and a flow channel through which air flows is defined by the flow channel formation member 130. In addition, the cap member 140 is fitted into the opening portion 133 provided in the top surface of the flow channel formation member 130, and the pressure adjustment spaces 101, which allow the space within the nebulizer kit to communicate with the exterior, are defined by the gap between the flow channel formation member 130 and the cap member 140.

To be more specific, the space within the case body 110 is partitioned into a central space and a peripheral edge space by the outside air introduction tube 134 provided in the lower area of the flow channel formation member 130; an outside air introduction channel 102 is defined by the inner side of the outside air introduction tube 134, whereas an aerosol transport channel 103 is defined by a region enclosed by the outer side of the outside air introduction tube 134 and the case body 110.

The outside air introduction channel 102 is a flow channel that leads outside air that has flown in from the pressure adjustment spaces 101 to the atomizing area M, whereas the aerosol transport channel 103 is a flow channel that leads the aerosol produced at the atomizing area M to the aerosol discharge port 132.

Meanwhile, the case body 110 according to the present preferred embodiment includes a wall surface 110b on the side of the case body 110, which encloses the outside air introduction tube 134, that is opposite to the side on which the aerosol discharge port 132 is provided, when viewed from the atomizing area M.

The wall surface of the case body 110 on the side on which the aerosol discharge port 132 is provided when viewed from the atomizing area M preferably has an approximately semicircular shape, and a straight line portion a planar surface when viewed three-dimensionally) is provided in the wall surface of the case body 110 on the opposite side as the side in which the aerosol discharge port 132 is provided, when viewed from the atomizing area M.

By providing the wall surface 110b including the straight line portion in the case body 110, the wall surface 110b serves as a barrier, making it possible to actively change the flow of the aerosol from flowing from the outside air introduction channel 102 in a direction moving away from the aerosol discharge port 132 to a direction moving toward the aerosol discharge port 132.

Meanwhile, the area (volume) of the opening located toward the side of the aerosol discharge port 132 when viewed from the atomizing area M is greater than the area (volume) of the opening located on the opposite side as the aerosol discharge port 132 when viewed from the atomizing area M. As a result, the discharge resistance of the aerosol is lower toward the aerosol discharge port 132 and greater on the opposite side as the aerosol discharge port 132. Accordingly, the aerosol is discharged more toward the aerosol discharge port 132.

Figure 7:
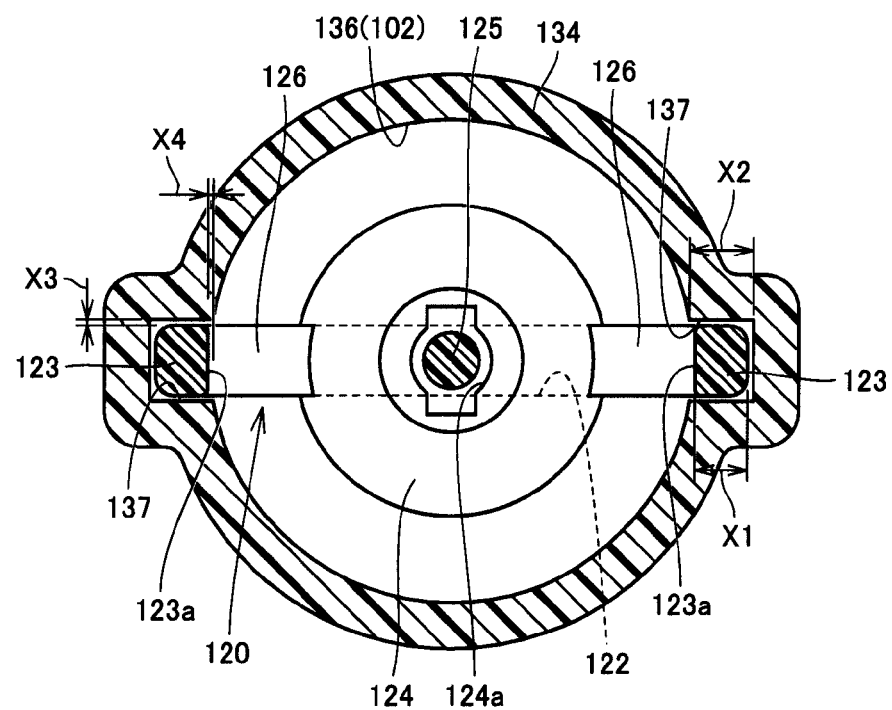
FIG. 7 is a vertical cross-sectional view taken along the VII-VII line in FIG. 5.
Figure 8:
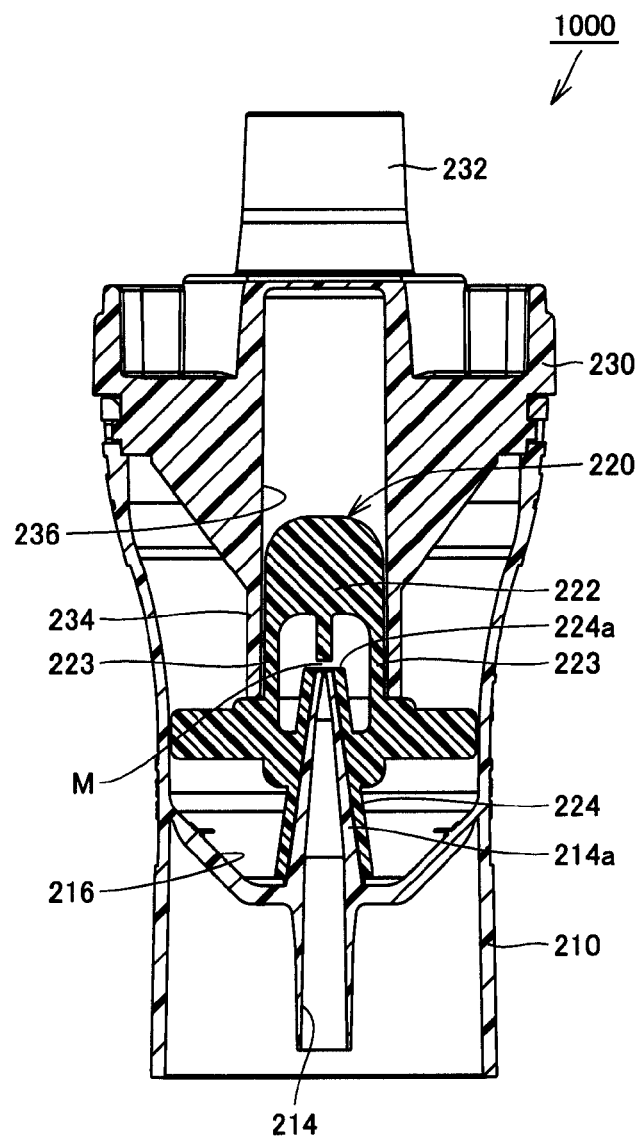
FIG. 8 is a cross-sectional view of a typical nebulizer kit.

Here, a characteristic configuration of the atomizing area formation member 120 and the outside air introduction tube 134 according to the present preferred embodiment will be described with reference to FIGS. 5 and 7. Note that FIG. 7 is a vertical cross-sectional view taken along the VII-VII line in FIG. 5. Note also that FIG. 7 illustrates a state in which the liquid suction tube formation portion 124 of the atomizing area formation member 120 is mounted so as to cover the upper leading end area 114a of the compressed air introduction tube 114 (see FIG. 5), and in which the flow channel formation member 130 is attached to the upper area of the case body 110.

Long grooves 137 that extend in a direction approximately parallel to a cylinder axis 110d of the case body 110 are formed in an inner circumferential surface 136 of the outside air introduction tube 134. The long grooves 137 preferably have a groove shape that is recessed outward in the radial direction of the outside air introduction tube 134 from the inner circumferential surface 136 of the outside air introduction tube 134. The long grooves 137 according to the present preferred embodiment are preferably provided in two locations directly opposite from each other, and are preferably formed so that the shape of the inner peripheral surface of the long grooves 137 is greater than the outer shape of the baffle support portions 123 of the atomizing area formation member 120.

The upper area of the atomizing area formation member 120 (that is, the baffle 122, portions of the baffle support portions 123, and so on) extends to within the outside air introduction tube 134 (see FIG. 6), and the baffle support portions 123 are contained within the long grooves 137 (see FIG. 7). A surface 123a on the inner peripheral side of the baffle support portions 123 may protrude slightly inward in the diametric direction from the inner circumferential surface 136 of the outside air introduction tube 134, or may be slightly recessed outward in the diametric direction from the inner circumferential surface 136 of the outside air introduction tube 134. It is preferable for the dimensions of the stated protrusion defined by the surface 123a and the inner circumferential surface 136, or the dimensions of the recess defined by the surface 123a and the inner circumferential surface 136 (a dimension X4, in FIG. 7), to be smaller than a width X3 of a gap between the baffle support portions 123 and the long grooves 137 in the vertical direction shown in FIG. 7.

Preferably, the surface 123a on the inner peripheral side of the baffle support portions 123 and the inner circumferential surface 136 of the outside air introduction tube 134 are in an approximately flush relationship. To achieve such an approximately flush relationship, it is preferable for a thickness X1 of the baffle support portions 123 in the diametric direction to be approximately equal to a groove depth X2 of the long grooves 137 in the diametric direction.

By configuring the atomizing area formation member 120 and the outside air introduction tube 134 as described above, a drop in the efficiency at which the aerosol is produced and discharged due to the mist particles or aerosol produced at the atomizing area M (see FIG. 6) collecting on the baffle support portions 123 is prevented. According to the nebulizer 1 and the nebulizer kit 100, it is possible to efficiently produce and discharge an aerosol.

It is further preferable for the outer shape of the baffle support portions 123 and the shape of the inner peripheral surface of the long grooves 137 to be formed so as to fit with each other, and for the configuration to be such that the baffle support portions 123 fit into the long grooves 137 when the baffle support portions 123 are contained within the long grooves 137. Meanwhile, in order to more strongly fit (press-fit) the baffle support portions 123 into the long grooves 137, one of the (members that configure the) baffle support portions 123 and the long grooves 137 may be configured of a resin (for example, an elastomer) having a lower hardness than the other of the (members that configure the) baffle support portions 123 and the long grooves 137. Note that configuring the (member that configures the) long grooves 137 from an elastomer or the like includes a partial configuration in which only the periphery of the long grooves 137 in the outside air introduction tube 134 that configures the long grooves 137 are configured from an elastomer or the like through insert molding, for example.

In addition, in order to more strongly fit (press-fit) the baffle support portions 123 into the long grooves 137, one of the outer shape of the baffle support portions 123 and the shape of the inner peripheral surface of the long grooves 137 may be configured in a tapered shape that narrows toward the upper end thereof, and the other of the baffle support portions 123 and the inner peripheral surface of the long grooves 137 may be configured in a column shape (a square column shape, a circular column shape, or the like). In the case where the shape of the inner peripheral surface of the long grooves 137 is configured in a tapered shape that narrows toward the upper side using a metal mold, the tapered shape can be formed easily by pulling the metal mold downward from the long grooves 137.

By fitting (press-fitting) the baffle support portions 123 into the long grooves 137, the flow channel formation member 130 can be removed from the case body 110 when the case body 110, the atomizing area formation member 120, the flow channel formation member 130, and the like are separated from each other, while the atomizing area formation member 120 remains held in the outside air introduction tube 134. It is thus possible to prevent the atomizing area formation member 120 from being dropped, damaged, or lost at the time of disassembly.

The atomizing area formation member 120 according to the present preferred embodiment includes two baffle support portions 123 in a positional relationship where the baffle support portions 123 face each other, and the two long grooves 137 are provided in the inner circumferential surface 136 of the outside air introduction tube 134 in correspondence therewith. The atomizing area formation member 120 may include one or more baffle support portions 123, and one or more long grooves 137 may be provided in the inner circumferential surface 136 of the outside air introduction tube 134 in correspondence therewith.

The foregoing has described exemplary preferred embodiments of the present invention, but it should be noted that the preferred embodiments disclosed above are to be understood as being in all ways exemplary and in no way limiting. The scope of the present invention is defined by the scope of the appended claims, and all changes that fall within the same essential spirit as the scope of the claims are intended to be included therein as well.

Further, while preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A nebulizer kit comprising:

a closed-ended, approximately cylindrical case body that includes an opening in an upper end, within which an aerosol is produced;

a cover-shaped flow channel formation member that is attached so as to cover the opening;

an outside air introduction tube, provided within the case body so as to hang downward from a base surface of the flow channel formation member, including a long groove provided on an inner circumferential surface;

a compressed air introduction tube, provided below the outside air introduction tube within the case body, including an upper leading end area that extends toward an interior of the outside air introduction tube; and an atomizing area formation member including a liquid suction tube formation portion including an opening portion formed in an apex thereof, a baffle located above the opening portion, and a baffle support portion that extends from an outer surface of the liquid suction tube formation portion toward a side area of the baffle; wherein the baffle support portion is contained within the long groove of the outside air introduction tube so that the flow channel formation member is attached to the case body and the liquid suction tube formation portion of the atomizing area formation member is mounted so as to cover the upper leading end area of the compressed air introduction tube.

2. The nebulizer kit according to claim 1, wherein a surface on an inner peripheral side of the baffle support portion and the inner circumferential surface of the outside air introduction tube are approximately flush when the baffle support portion is contained within the long groove of the outside air introduction tube.

3. The nebulizer kit according to claim 1, wherein an outer shape of the baffle support portion is formed so as to correspond to the shape of an inner peripheral surface of the long groove; and
the baffle support portion is fitted into the long groove when the baffle support portion is contained within the long groove.

4. A nebulizer comprising:
a nebulizer kit comprising:
  a closed-ended, approximately cylindrical case body that includes an opening in an upper end, within which an aerosol is produced;
  a cover-shaped flow channel formation member that is attached so as to cover the opening;
    an outside air introduction tube, provided within the case body so as to hang downward from a base surface of the flow channel formation member, including a long groove provided on an inner circumferential surface;
    a compressed air introduction tube, provided below the outside air introduction tube within the case body, including an upper leading end area that extends toward an interior of the outside air introduction tube; and
    an atomizing area formation member including a liquid suction tube formation portion including an opening portion formed in an apex thereof, a baffle located above the opening portion, and a baffle support portion that extends from an outer surface of the liquid suction tube formation portion toward a side area of the baffle;
  a main body including a compressor that discharges compressed air; and
  a compressed air tube portion including one end connected to the compressor and another end connected to the case body; wherein
  the baffle support portion is contained within the long groove of the outside air introduction tube so that the flow channel formation member is attached to the case body and the liquid suction tube formation portion of the atomizing area formation member is mounted so as to cover the upper leading end area of the compressed air introduction tube.

5. The nebulizer kit according to claim 1, wherein an axis of the outside air introduction tube and an axis of the opening portion of the liquid suction tube formation portion are in alignment with each other.

6. The nebulizer kit according to claim 4, wherein an axis of the outside air introduction tube and an axis of the opening portion of the liquid suction tube formation portion are in alignment with each other.

* * * * *